United States Patent [19]
Berg

[11] Patent Number: 5,253,168
[45] Date of Patent: Oct. 12, 1993

[54] SYSTEM FOR CREATIVE EXPRESSION BASED ON BIOFEEDBACK

[76] Inventor: Jacqueline L. Berg, 930 Judson 2W, Evanston, Ill. 60202

[21] Appl. No.: 804,073

[22] Filed: Dec. 6, 1991

[51] Int. Cl.⁵ .................. G06F 15/00; A61B 5/08; A61B 5/05
[52] U.S. Cl. .................. 364/413.01; 364/413.04; 128/725; 128/734
[58] Field of Search .............. 364/413.01, 413.02, 364/413.03, 413.04, 413.13; 128/732, 733, 696, 736, 734

[56] References Cited
U.S. PATENT DOCUMENTS

| | | | |
|---|---|---|---|
| 4,461,301 | 7/1984 | Ochs | 128/630 |
| 4,632,126 | 12/1986 | Aguilar | 128/732 |
| 4,984,158 | 1/1991 | Hillsman | 364/413.04 |

Primary Examiner—Roy N. Envell, Jr.
Assistant Examiner—Khai Tran
Attorney, Agent, or Firm—Hill, Steadman & Simpson

[57] ABSTRACT

A system for allowing an individual to express themself in a creative manner by using biofeedback signals to direct imaging and audio devices.

3 Claims, 4 Drawing Sheets

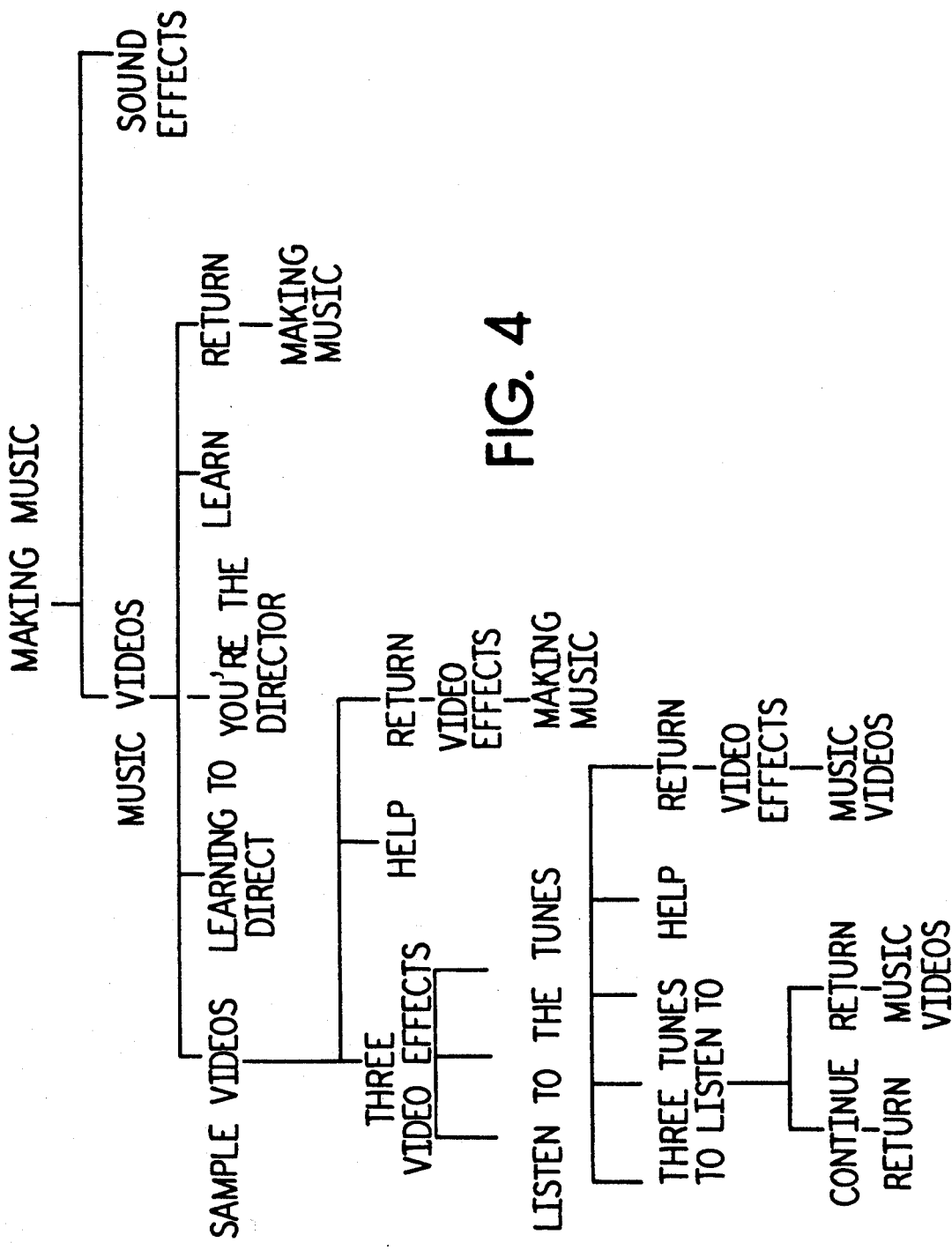

SYSTEM FOR CREATIVE EXPRESSION BASED ON BIOFEEDBACK

BACKGROUND OF THE INVENTION

The present invention generally relates to methods and apparatus for sensing physiological events, hereinafter referred to as biorhythms. Additionally, the invention relates to computer based systems for driving imaging and audio devices. Yet further, the invention relates to real time interactive multimedia computer based systems.

It is known to sense biorhythms and to generate signals relating thereto so that a subject whose biorhythms are being sensed can receive feedback relating thereto. It is known to use this feedback to effect control over the bodily function or activity generating the biorhythm. For example, it has been known that subjects can effect control over the heart rate by being provided with feedback relevant thereto. Further, subjects have been known to be able to control their skin resistance while receiving continuous measurements thereof.

SUMMARY OF THE INVENTION

The present invention provides a system by means of which a subject can utilize biorhythm feedback to generate creative expressions. Furthermore, the invention provides a system by means of which a subject can be provided with information concerning the interrelationship between various physiological events and activities.

To these ends, in an embodiment, the invention provides a computer system to which are coupled at least one sensor operative to sense at least one biorhythm, a video camera, a video monitor, and an audio system, as well as computer programs stored in the computer which are operative to process signals from the biorhythm sensor and the video camera to generate video and audio signals incorporating information relating to the sensed biorhythms. The computer programs preferably provide for selection of one of a variety of physical and/or mental activities which is then monitored to display the affect of the selected activity on the sensed biorhythm.

In an embodiment, the invention provides that the biorhythm sensor is a pulse sensor.

In an embodiment, the invention provides that the biorhythm sensor is a galvanic skin response sensor.

In an embodiment, the invention provides that the computer programs are operative to process a real time video image of the subject.

These and other features of the invention will become clearer with reference to the following detailed description of the presently preferred embodiment and drawing.

BRIEF DESCRIPTION OF THE DRAWING

FIG. 4 illustrates a program tree of another portion of the program of FIG. 2.

DETAILED DESCRIPTION OF THE PRESENTLY PREFERRED EMBODIMENT

Figure 1:
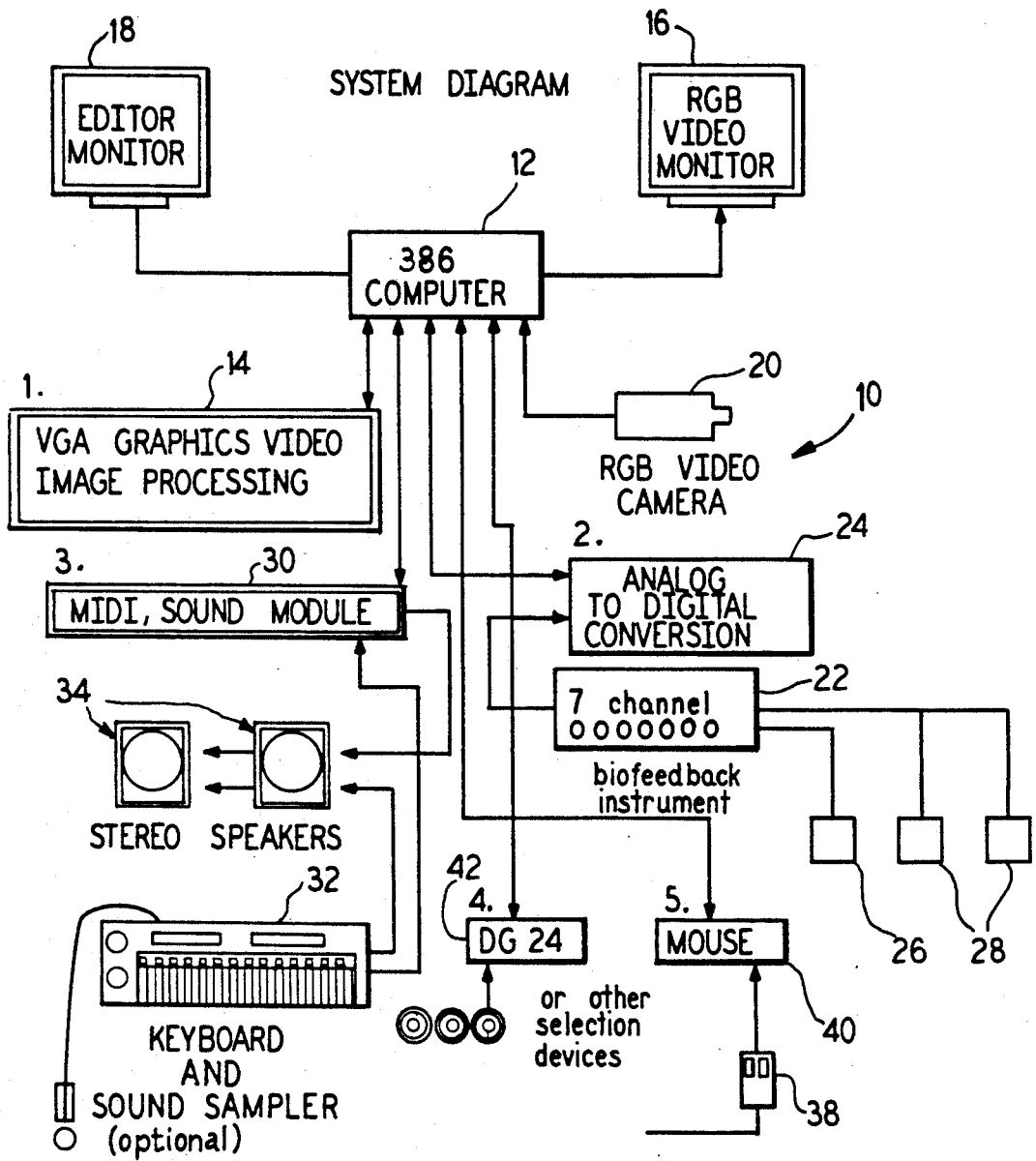
In FIG. 1, there is illustrated in block diagram form a computer based system for receiving biorhythm signals from a subject and providing for creative expression feedback.

In accordance with the invention, a system is provided wherein a subject is provided with creative expression feedback relating to sensed biorhythms. By controlling the relevant biorhythms, the subject can alter the creative expression feedback thereby to obtain an understanding of various bodily activities as well as the interrelationships between them.

To these ends, the present system provides a real time interactive multi-media hardware/software system. This system is based on a human-machine interface of biorhythms which drive imaging and audio devices. Together, the technologies involved offer a unique configuration and application of tools for learning through creative expression.

With this interdisciplinary approach, an individual can use psychological output sensors to reflect thoughts and emotions. Further, a subject can interactively learn to relate psychological outputs to their own emotions and thoughts, as well as the imaging and audio feedback input.

The system is based on the biofeedback principle of learning which states that one can learn to change biological responses when one receives back visual or audible information about that response. This principle provides a dynamic, innovative approach to learning and healing. The method encourages the subject to choose a mental and physical state through positive reinforcement.

As illustrated in the drawing, in a preferred embodiment, a system 10 for providing creative expression feedback relating to biorhythms preferably incorporates a microprocessor 12 such as the so-called 386 class of microprocessor for personal computers. Of course it is known that the reference to 386 relates to the 80386 chip that is produced by Intel Corporation and its imitations or compatibles.

To the microprocessor 12 are coupled a graphics video image processing module 14, preferably a VGA graphics board. The VGA graphics module 14 is used to generate alterable video signals suitable for driving a color video monitor 16 also coupled to the microprocessor 12.

Additionally provided is an editor monitor 18 via on which, as will be explained more fully below, selections or options in a main program can be displayed and then edited. Thus, an overseer such as a therapist or other medical person can configure the system for the subject.

Also coupled to the microprocessor 12 is a color video camera 20 used to obtain a continuous real time video image of the subject who would be using the system 10. The real time image of the subject is displayed on the video monitor 16 as will be described below so that the image can be altered and controlled in view of sensed biorhythms thereby to provide a creative feedback relating to the sensed biorhythms.

To receive signals relating to the biorhythms, there is included a seven channel biofeedback device 22 coupled to the microprocessor 12 by means of an analog-to-digital converter 24. The biofeedback device 22 in turn preferably is coupled to a pulse sensor 26 and two small galvanic skin response sensors 28. Of course, other inputs for ECG, EKG, etc. type devices can be provided.

For further creative input, as will be described in further detail below, there is included a musical instrument digital interface (MIDI) 30 used for coupling a musical instrument such as a synthesizer to the microprocessor 12. In the exemplary embodiment, there is included a synthesizer 32 coupled to the MIDI 30. At the same time, there are included speakers 34 coupled to both the MIDI 30 and the synthesizer 32.

In addition to the foregoing, a mouse 38 is coupled to the microprocessor via a mouse driver 40 for alternate input to the microprocessor 12. The mouse is used for selection of creative expression options presented to the subject.

Yet further, the system 10 is provided with a digit switch console 42, preferably of the type known as DG24. Selections described below then can be made via appropriate actuation of digital switches on the console 42.

It can be appreciated that the analog-to-digital converter board 24, the musical instrument digital interface board 30, mouse driver board 40, and digital graphics board 42 can be constructed as computer boards so that the microprocessor and these boards are incorporated into a single personal computer cabinet.

With the foregoing overall description in mind, the manner in which the system is used is discussed.

In the illustrated embodiment, the pulse sensor 26 and two small galvanic skin response sensors 28 are placed on three of a subject's fingers also referred to hereinafter in female gender form. The subject is asked not to move her hand.

When the subject first enters the software, i.e., starts-up the relevant creative expression computer program, a large colorful main graphic menu is presented on the monitor 16 which offers three activities to work with: "Design Your Image," "Composing Music," "Painting With Lasers," and "Help." This and all other graphic menus described below are overlayed onto a live processed video image of the subject also presented on the monitor 16. The video image of the subject is altered by special effects provided by the image processor 14 which change with each selectable activity.

If the subject first picks "HELP," then a brief introduction about the various activities is presented and then a new screen will appear on the monitor 18 with a display of all icons and their meaning. There is a "HELP" icon on every menu which calls up instructions or directions for that specific part of the activity. After reviewing the information, the subject can close or exit the HELP routine and again be presented with the main menu.

If the subject chooses "Design Your Image," which is the video image processing activity, she is now taken into another menu which asks her to choose: "Design Effects," "Learning to Design," "Express Yourself," and "HELP." If she chooses "Design Effects," she can preview each of the special effects that will b correlated with her bio-rhythm activity.

It can be appreciated that the various design effects are provided by the image processing module 14. Thus, the different effects available in reality are a function of the particular module used. For ease of understanding only two are discussed herein.

"Learning to Design" is the learning tutorial for this activity. It is here that the user can learn how to change her bio-rhythms and thus redesign the video image of herself displayed on the monitor 18 with each of the special effects. To accomplish this, the next menu asks her to pick a special effect to work with. Since she will have previewed all effects, she can pick the design effect which was most interesting or attractive to her.

The next menu asks which bio-rhythm she wants to work with. She can choose between "Heart Rate" and "Skin Resistance." If she chooses "Heart Rate," then she is asked if she wants to use a physical or mental activity. If she chooses "Physical Activity," a menu will appear with selectable exercises, for example, the following exercises: Breathe Normal, Hold Your Breath, Breathe Deep and Slow, Breathe Fast, and Hold Up Your Arms. If she chooses "Hold Your Breath," the software will then hold the following information: the user wants to work with "Heart Rate," she will be using the physical exercise "Breathe Fast," and, for example, "Design Effect #3," which makes a split mirror image of her face, moves and changes color.

When the first tutorial begins, a live video screen comes up with the subject's face changed by the special effect. On the far right side of the screen is an opaque column for a heart icon to appear. The prompt "Breathe Fast" appears on an opaque strip at the bottom of the screen and EXIT if she wants to return.

The subject then would begin to breathe fast. If her heart rate increases, the heart icon appears with an arrow pointing up. The video effect will turn her face red and make an upward movement. If her heart rate decreases, the heart icon will appear with the arrow pointing down, her image will become blue and move downward. If it remains the same, the heart icon has no arrows, the effect turns yellow and does not move.

As a result of this interaction, the subject should come to understand that breathing fast changes her heart rate in a certain way and that it produces a certain change in that special effect. She can choose to go back to this lesson as many times as necessary to understand the correlations.

After this lesson, she can continue to work with each of the remaining special effects using "Breathe Fast" and "Heart Rate." Further, she can go back and choose another "Physical Exercise" or "Mental Exercise." Yet further, she can choose to work with "Skin Resistance" rather than "Heart Rate."

For example, in another lesson, the subject can chose "Skin Resistance," the mental exercise, "Think of a Soft Touch," and "Design Effect #5" which strobes her image slower or faster and changes its color. When her skin response increases, a finger icon will appear with an arrow pointing upward. The effect turns pink and her image will strobe faster.

Since the changes in each special effect happens in real time (as her skin resistance changes her image changes) the effects can change rapidly or slowly depending upon her biorhythm trend. The icons continually keep her informed about the bio-rhythm trend. These visual changes reinforce the subject to make a conscious effort to change her bio-rhythms. She may like certain effects, such as the one associated with her heart rate increasing, or, she may just like the effects to change rapidly. In the latter case, she can alternately increases and decreases her heart rate. Thus, a biofeedback learning loop is provided.

For both Heart Rate and Skin Response, there can be 72 choices each. Each special effect can be used with any one of, for example, six physical exercises or any one of six mental exercises. For example, six (6) effects×twelve (12) exercises =seventh-two (72) choices. Thus, is the subject wishes to, she could learn to manipulate 144 special effects changes using her heart and skin bio-rhythms.

The final stage of the "Design Your Image" activity is "Express Yourself." In this branch, the subject uses both her heart rate and skin response activity and each controls its own special effect. The subject chooses the special effect she wants for her heart and the one she wants for her skin. She can use any of the mental or physical exercises to make changes in her bio-rhythms. Using the examples above, her heart can change a mirror effect, with movement and color; and her skin can change the effect in terms of strobe speed and color.

This "creative" part of the activity gives the subject freedom to play with the effects at will and for any length of time. She can go back and choose another set of effects for her pulse and skin response at any time.

To make a permanent creative record of her work, the video output can be taped as it is happening. To this end, a video recorder can be coupled to the video image signal when she stops to change to other special effects, the tape can be stopped. It is then resumed when she begins the next session so there is an uninterrupted sequence of imagery (manual control of the tape deck is necessary). This final video tape is her personal creative imaging piece which she can view at her pleasure in the future. It can also be used by the therapist to make therapeutic evaluations of the subject's progress.

There are two other activities that operate in a similar way so no detailed explanation is included here. These activities are "Composing Music" and "Painting With Lasers." "Composing Music" uses the MIDI interface 30. The subject preferably selects between three tunes and her bio-rhythms control what instruments play the tune. Her bio-rhythms are actually a "sequencer" since as many as six instruments could be activated to play at once using both pulse rate and skin resistance.

The output of the MIDI interface 30 also is output into the image processor 14. Bass tones from the MIDI interface 24 can cause certain special effects to change. Therefore, as the subject is listening and changing her bio-rhythms in view of the output of the MIDI interface 30, she also can watch the monitor 18 with changing special effects as well. Thus, a real multi-media environment working in real time is provided.

Another section of the "Making Music" activity is the digital sampling in of sound effects which the subject makes or chooses. She can play with these sound effects—change them or put them together—in a creative way. These sessions can be audio taped in the same way as video taping of the visual effects. If the facility in which the system 10 is in use has in-house editing, the audio can be dubbed onto her video imagery tape to mix the two medias.

"Painting With Lasers" provides six sinusoidal waveforms to choose from. Bio-rhythms change the form, color, rotation and movement of these waveforms. The sinusoidal waveforms can be projected onto a small insert screen where a prerecorded video tape of the subject's face is being displayed. If the subject music is dubbed onto the video tape, a real time, multi-media event takes place with this combining and overlapping of media.

For the therapist there are two sections which the subject may or may not participate in. The first is a separate "Editor" which allows the therapist to modify the activities to meet specific goals for an individual subject. If the subject has a certain behavior that the therapist feels is hindering the individual, she can modify an activity to reinforce a positive behavior.

In the "Editor," the therapist can type in simple statements (via prompts) which will alter the activity to operate in a specific way. For instance, she may ask that only certain video special effects be offered based on their design and color. She may want to limit a menu selection or change its sequence. She could write special prompts into the mental or physical exercises which she believes would most quickly change the subject's bio-rhythms.

There are hundreds of special effects that the therapist can work with, preferably only six are placed in the "Design Effects" for the subject to choose from. Similarly, the subject preferably picks from six tunes and six instruments, but the therapist can sample in all the tunes she wants and there are as many as 100 instrument sounds in a MIDI sound module. The "Editor" opens up the system to an unlimited variety of image and sound possibilities. The system is also open to other channels of biofeedback signals such as EMG, EEG, and EKG.

One further section is called "Graphs." This produces real time line graphics of the bio-rhythm trends. Icons of the heart and finger also appear as the bio-rhythm changes. This section is directed towards the therapist to make on the spot evaluations such as the pen charts on an electroencephalograph.

The primary user support would be therapists, doctors, psychologists and technical/medical assistants. These individuals would assist or direct a mentally retarded patient during his/her time with an activity. Typically, a mentally retarded individual would not be able to learn how to use the activities alone. However, after guidance, certain individuals could run the activities without much assistance. If they have severe physical handicaps, there are specialized menu selection hardware devices available on the market that can be incorporated into the described system.

Again, the goal of these activities is to offer individuals with severe developmental disabilities an opportunity to express themselves artistically and to encourage positive reinforcement of behavior. Typically, such individuals are not able to access traditional art making tools because of mental or physical handicaps. Yet, they still need a method of making creative choices and artistic statements about themselves. Through the use of bio-feedback, the therapist is able to provide a dynamic, positive learning opportunity for their patients.

Figure 2:
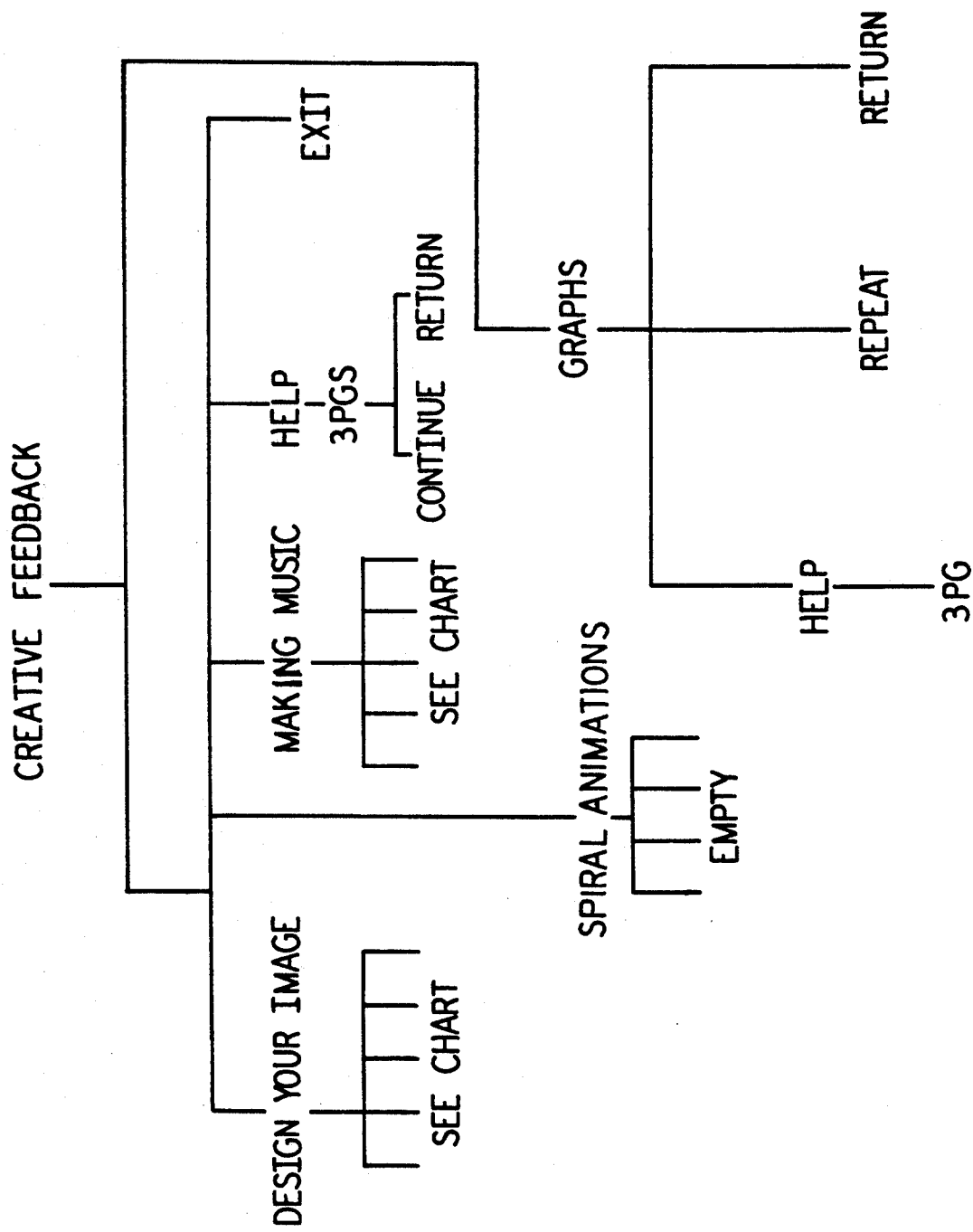
In FIG. 2 there is illustrated a program tree for a main menu portion of a computer program for a system embodying principles of the invention.
Figure 3:
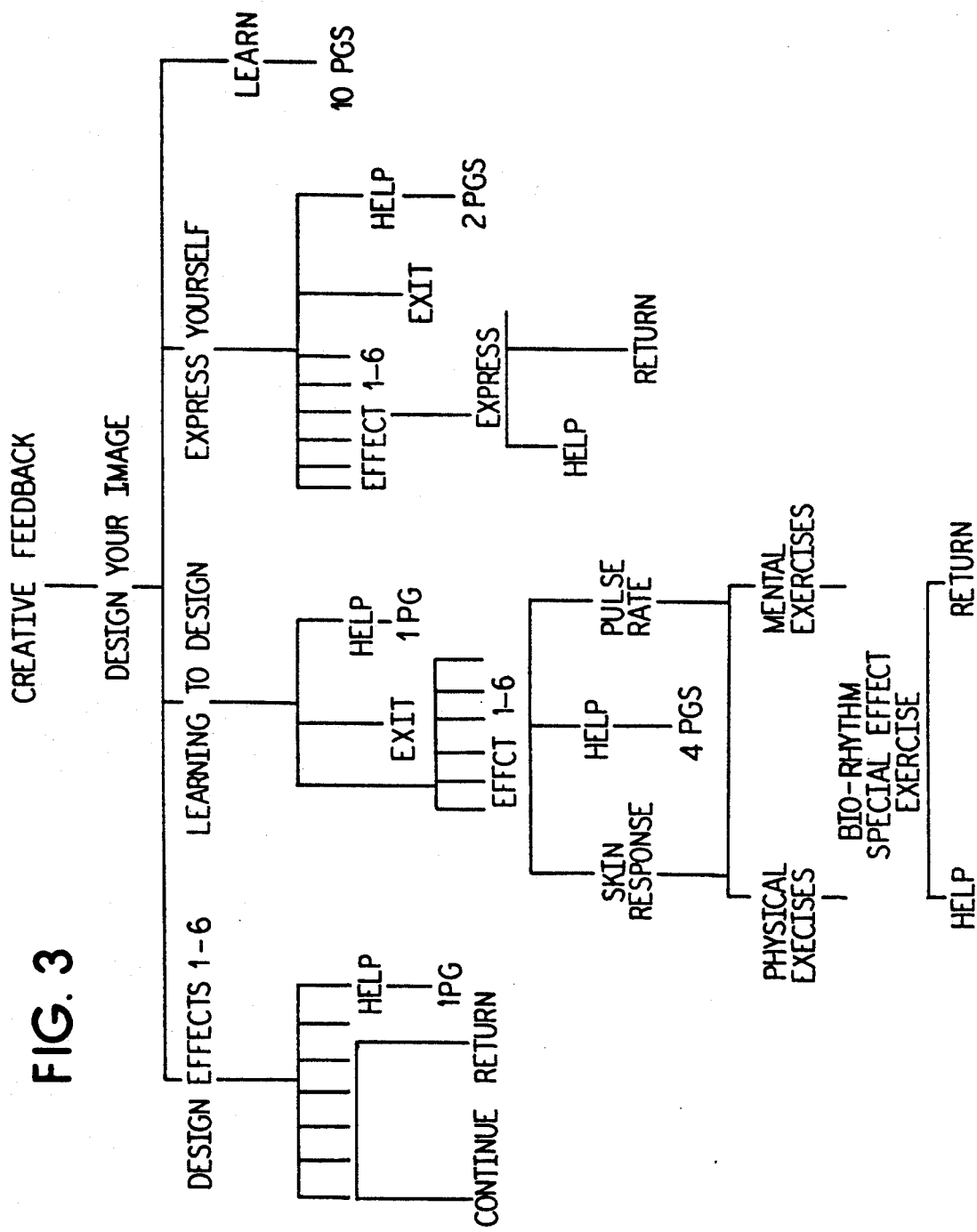
FIG. 3 illustrates a program tree of a portion of the program of FIG. 2.

In FIGS. 2-4, there is illustrated a program tree generally outlining the selections available to a subject and/or therapist during the course of operation of the system. This tree should enable one of ordinary skill in the art to readily understand the system structure of the computer program used to enable the subject to operate the sysetm 10.

While preferred embodiments have been shown, modifications and changes may become apparent to those skilled in the art which shall fall within the spirit and scope of the invention. It is intended that such modifications and changes be covered by the attached claims.

What is claimed is:

1. A system for allowing an individual to express themself in a creative manner by employing physiologic feedback signals, comprising:

a programmable digital processor with a memory attached thereto;

at least one physiologic sensor operatively configured to sense at least one physiological event and to generate a physiological signal relating thereto a video camera operatively coupled to the digital processor to provide thereto a real time video signal;

a video monitor operatively coupled to the digital processor;

a data input device operatively coupled to the digital processor; and means included in said programmable digital processor for processing the video signal, the at lest one physiological signal, and data from the data input device to produce a real time video image on the video monitor whose character changes under the control of the physiological event, said means for processing being programmed to include a plurality of selectable special effects which change the character of the video image.

2. A biofeedback system, comprising:

means for sensing at least one physiological event of a subject and generating a biorhythm signal relating thereto;

means for generating a video signal relating to the subject;

display means for displaying a video image; and means for processing the video signal and biorhythm signal to generate an image signal which is used to drive the display means to produce a video image, the means for processing being programmed to allow for selection of characteristics of the image signal that can be altered, the means for processing altering the image signal characteristics under the control of the biorhythm signal, the means for processing being programmed to superimpose graphical information on the video image.

3. A system for allowing an individual to express themself in a creative manner by employing physiological feedback signals, comprising:

a digital processor with a memory attached thereto;

a plurality of physiological sensors operatively configured to sense different physiological events to generate physiological signals relating thereto;

a video camera operatively coupled to the digital processor to provide thereto a real time video signal;

a video monitor operatively coupled to the digital processor;

a data input device operatively coupled to the digital processor;

a musical sound-generating device operatively coupled to the digital processor;

wherein said digital processor is programmed to process the video signal, the physiological signals, the real time video signal data from the data input device to produce a real time video image on the video monitor whose character changes under the control of one or more of the physiological events, the digital processor being programmed to allow for selection of any number of special effects on the real time video image such that a selected physiological event will drive a selected special effect thereby to cause a selected character change of the real time video image, the digital processor being programmed to process the physiological signals to selectively control generation of music on the musical sound-generating device.

* * * * *